United States Patent [19]

Broughton et al.

[11] Patent Number: 5,022,854
[45] Date of Patent: Jun. 11, 1991

[54] ORTHODONTIC BRACKET

[75] Inventors: Dan Q. Broughton, Vista; Nicholas O. Norris, Oceanside, both of Calif.

[73] Assignee: Ortho Organizers, San Marcos, Calif.

[21] Appl. No.: 549,259

[22] Filed: Jul. 5, 1990

Related U.S. Application Data

[63] Continuation of Ser. No. 285,208, Dec. 16, 1988, abandoned.

[51] Int. Cl.$^5$ .............................................. A61C 3/00
[52] U.S. Cl. ...................................................... 433/8
[58] Field of Search ...................... 433/8, 9, 10, 11, 12, 433/13

[56] References Cited

U.S. PATENT DOCUMENTS

| | | | |
|---|---|---|---|
| D. 302,588 | 8/1989 | Jones | D24/16 |
| 4,415,330 | 11/1983 | Daisley et al. | 433/8 X |
| 4,536,154 | 8/1985 | Garton, Jr. et al. | 433/8 |
| 4,659,309 | 4/1987 | Merkel | 433/9 |
| 4,819,316 | 4/1989 | Rossini et al. | 433/8 X |

FOREIGN PATENT DOCUMENTS

| | | | |
|---|---|---|---|
| 2520191 | 11/1975 | Fed. Rep. of Germany | 433/10 |
| 3700517 | 8/1987 | Fed. Rep. of Germany | 433/13 |

Primary Examiner—Cary E. Stone
Assistant Examiner—Nicholas D. Lucchesi
Attorney, Agent, or Firm—Fulwider, Patton Lee & Utecht

[57] ABSTRACT

The invention is directed to an orthodontic bracket assembly having a trapezoidal configuration for ease of positioning and aligning the bracket on the tooth. The bracket assembly comprises a pair of tie wings, each having non-parallel mesial and distal edges and further having an occlusal edge substantially parallel to the occlusal plane and to the sight line of the archwire slot. The edges of the tie wings form sight lines that intersect at a focal point located at the tip of the root tooth to assist in positioning the bracket. The edges of the tie wings also are substantially parallel to the tooth edges to assist in aligning and positioning the bracket on the tooth. Further, a V groove is provided along the longitudinal axis of the bracket and forms a sight line that also intersects the focal point to facilitate alignment of the bracket during mounting. The occlusal edge of the tie wings is parallel to the sight line of the archwire slot and both form sight lines that are substantially parallel to the edge of the tooth. The various sight lines forming a trapezoidal configuration for ease in positioning and aligning the bracket during mounting.

3 Claims, 3 Drawing Sheets

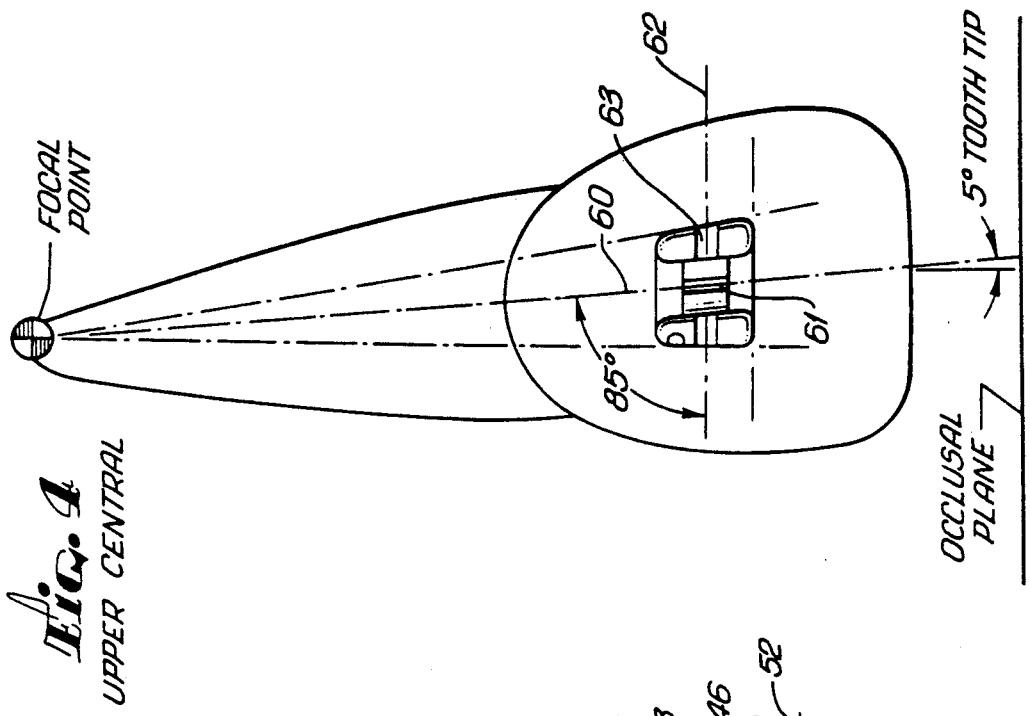
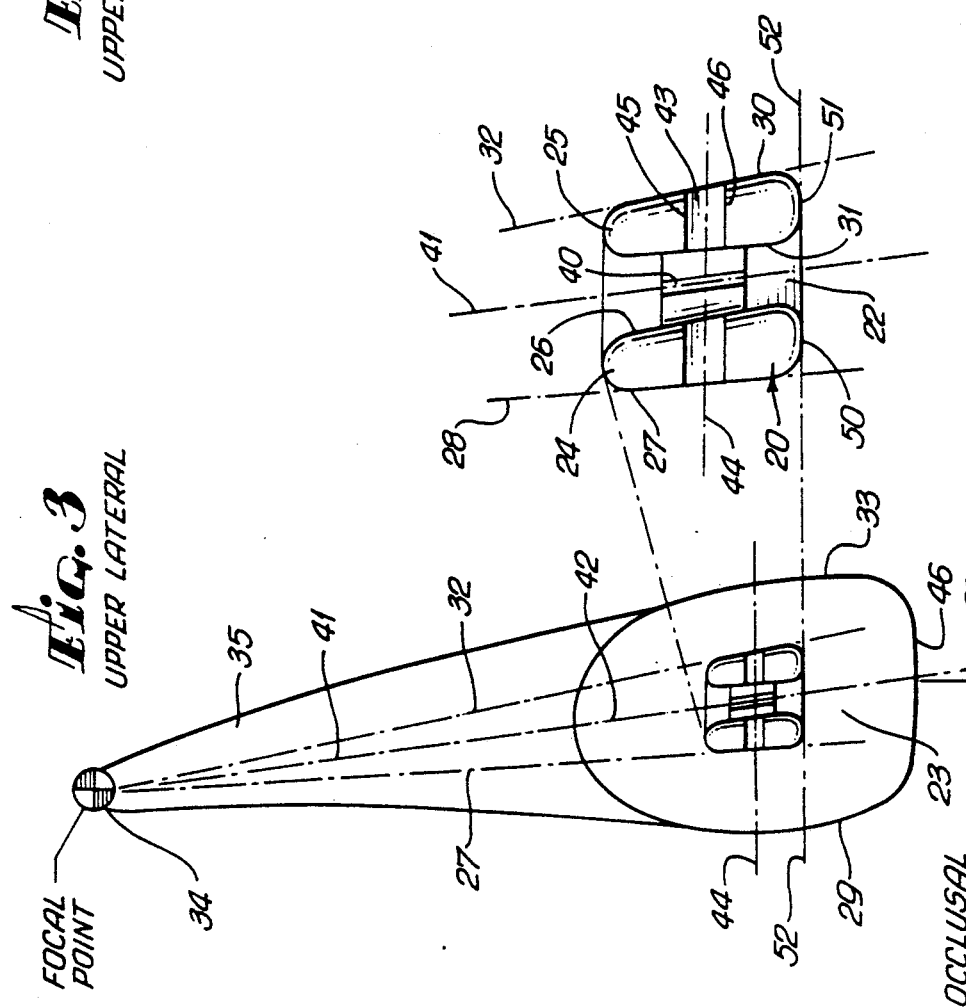

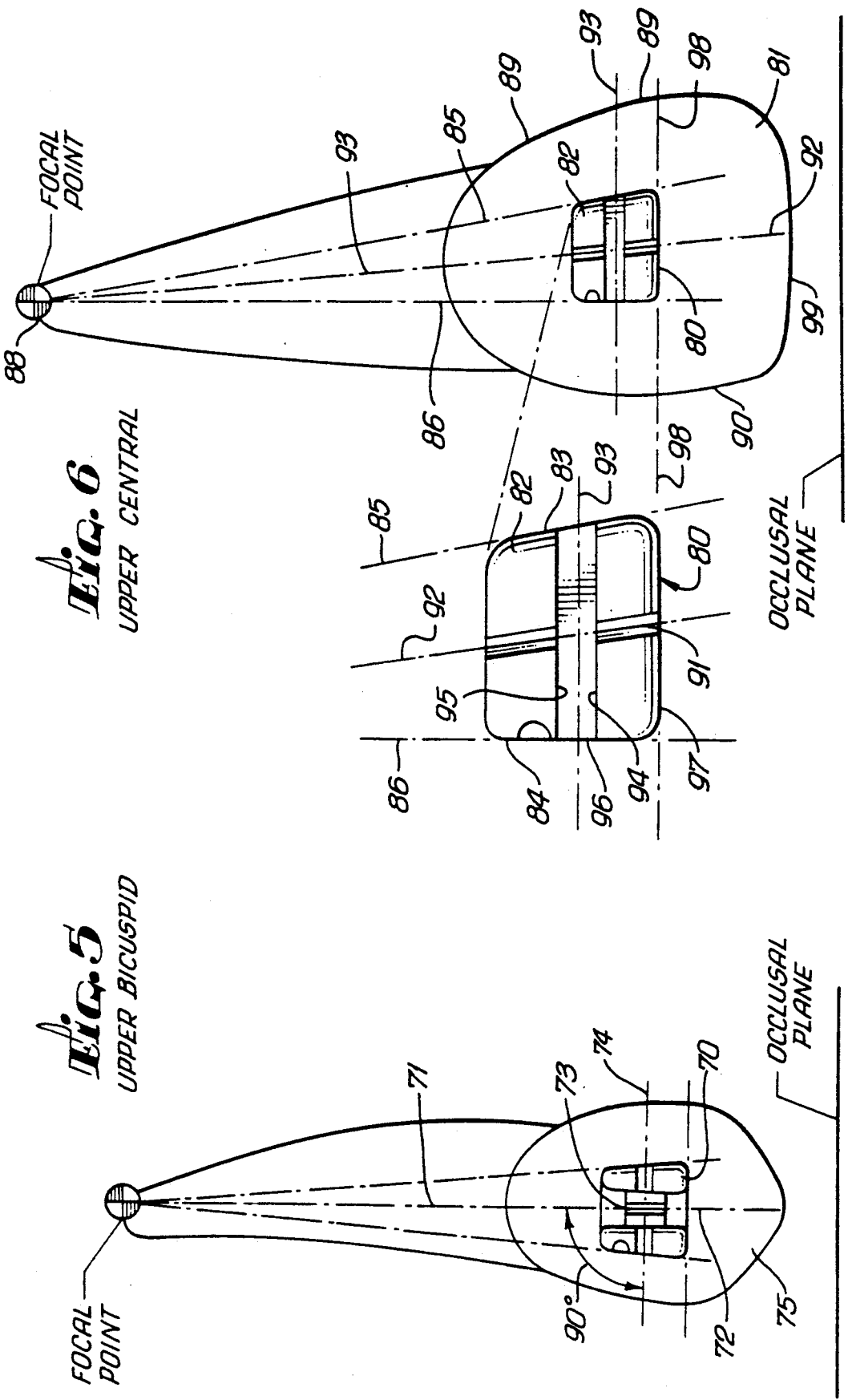

ORTHODONTIC BRACKET

This application is a continuation of application Ser. No. 285,208, filed Dec. 16, 1988, abandoned.

BACKGROUND OF INVENTION

The present invention relates generally to an orthodontic bracket having a trapezoidal configuration wherein sight lines on the bracket are utilized to facilitate alignment and positioning of the bracket on the tooth.

There are numerous tooth configurations and sizes which vary from one patient to the next. In most cases, however, the majority of people having malposed teeth have teeth which conform to certain profiles and sizes such that orthodontic brackets mounted on the teeth can also be standardized to correspond to certain tooth sizes and configurations.

At the same time brackets are being standardized, they are also becoming smaller. With the advance of higher quality casting and finishing processes the sizes of orthodontic brackets have gotten smaller for a number of reasons, several of which are to reduce the cost of raw materials and for aesthetic purposes so as to draw less attention to the wearer. Smaller brackets are also advantageous since they reduce irritation and pain to the patient caused by larger brackets and appliances.

With the advent of the smaller bracket designs there has occurred several disadvantages. For example, the amount of time a patient is in the chair while the orthodontist is mounting orthodontic brackets has increased. This not only increases the cost to the patient, but reduces the efficiency of the orthodontist and reduces the amount of time he might spend with other patients. Further, smaller sized brackets increase the likelihood of misalignment of the bracket in relation to the tooth thereby causing several more problems. Misalignment results in difficulty in mounting the archwire in the archwire slot of the bracket and may also cause undesired or unplanned movement of a particular tooth, resulting in a longer time for treatment to move the tooth to the proper position. Misalignment of a bracket in relation to the tooth and the archwire might even require removal of the bracket and remounting.

Certain prior art patents purport to have design features which facilitate alignment of the bracket on the tooth. One such patent, U.S. Pat. No. 4,415,330, discloses a bracket having a rhomboidal configuration which has edges that align, for example, with the occlusal plane and the crown long axis. The patent discloses tie wings having edges that are parallel to the crown long axis to assist in alignment during mounting of the bracket. Also, the occlusal and gingival tip of the tie wings are parallel to each other and to the occlusal plane again to facilitate alignment. The patent does not, however, have mesial and distal sides that are substantially parallel to the mesial and distal sides of the tooth upon which the bracket is mounted. Thus, with respect to the tooth configuration, the prior art patent ignores the shape of the tooth and its structural features.

The orthodontic bracket of the present invention was designed to obviate the problems in aligning and positioning a bracket on the tooth. It is thus an object of the present invention to provide an orthodontic bracket having a trapezoidal configuration to substantially conform to the shape of the tooth.

It is another object of the invention to provide an orthodontic bracket having a trapezoidal configuration wherein sight lines are used to increase the accuracy in aligning and positioning the bracket on the tooth.

It is a further object of the invention to reduce the amount of time that a patient is in the chair while the orthodontist is mounting brackets.

It is a still further object of the invention to provide an orthodontic bracket that will reduce the likelihood that an orthodontist will have to re-mount the bracket to correct for misalignment between the bracket and the tooth.

SUMMARY OF THE INVENTION

An orthodontic bracket having a trapezoidal configuration is provided wherein a distal tie wing has mesial and distal edges and an occlusal edge that is substantially parallel to an archwire slot, and a mesial tie wing has mesial and distal edges and an occlusal edge substantially parallel to the archwire slot. The distal edge of the distal tie wing and the mesial edge of the mesial tie wing, along with the occlusal edges and the midline of the archwire slot define a rhomboidal configuration. The distal edge of the distal tie wing and the mesial edge of the mesial tie wing forming sight lines which intersect at a focal point located substantially at the tip of the tooth root. Further, a sight line is provided which is approximately midway between the tie wings and substantially along the tooth axis such that the sight line intersects the mesial and distal sight lines at the focal point. The occlusal edges of the tie wings also form sight lines, as does the midline of the archwire slot, such that together these two sight lines are parallel to the occlusal edge of the tooth upon which the bracket is mounted. Thus, the present invention incorporates sight lines to facilitate not only alignment, but positioning of the bracket on the tooth for increased accuracy in mounting brackets.

DESCRIPTION OF THE DRAWINGS

FIG. 3 is a front elevational view of an upper lateral bracket assembly of the present invention depicting the various sight lines;

FIG. 4 is a front elevational view of an upper central tooth having one embodiment of the bracket assembly of the present invention mounted thereon;

FIG. 5 is a front elevational view of an upper bicuspid tooth having a bracket assembly mounted thereon and having 0° of tip; and FIG. 6 is a elevational view of an upper central tooth having a single wing bracket assembly mounted thereon and having 0° of tip.

DESCRIPTION OF THE PREFERRED EMBODIMENTS

Numerous variables are involved when an orthodontist is mounting orthodontic brackets on the teeth. Today's brackets are becoming smaller and more difficult to handle and, importantly, are becoming more difficult to properly align and position on the tooth. The bracket 10 of FIG. 1 reduces the alignment and positioning problems encountered with small brackets by providing various sight lines that are useful to the orthodontist in assuring proper bracket placement.

Figure 1:
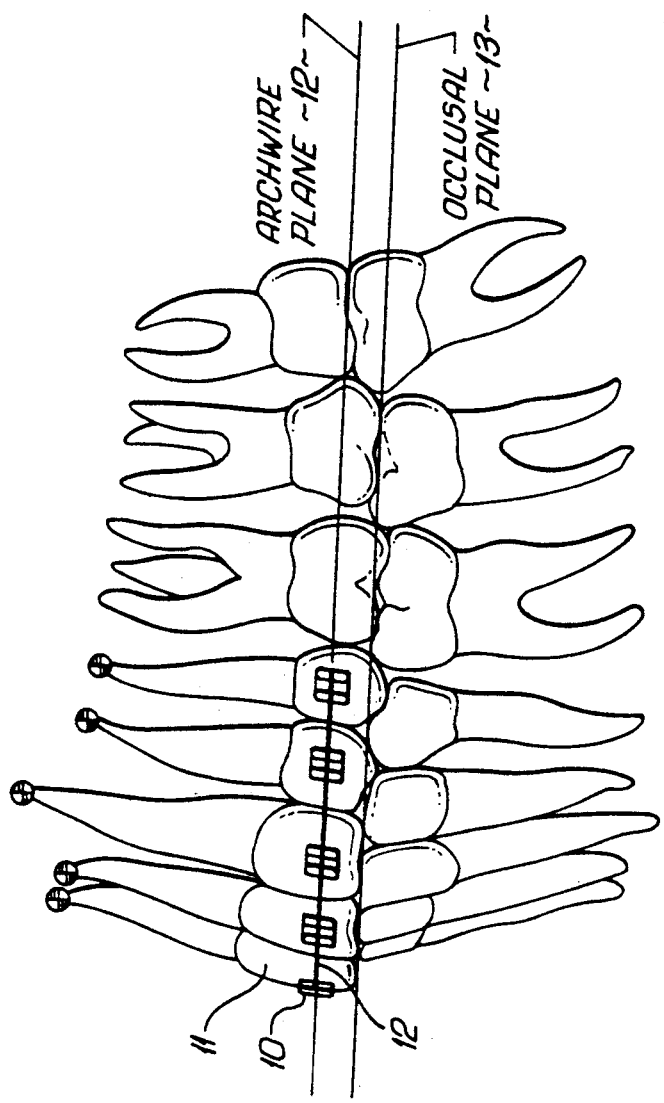
FIG. 1 is a side elevational view illustrating several bracket assemblies of the present invention mounted on the left side of the tooth structure.

The bracket 10 of the present invention is shown as it is mounted on the teeth 11 depicted in FIG. 1. Normally, brackets 10 will be mounted on teeth 11 by bonding, and each bracket 10 is interconnected by an archwire 12. It is preferred that the archwire 12 of the upper and lower jaw define a plane that is parallel to occlusal plane 13.

Figure 2:
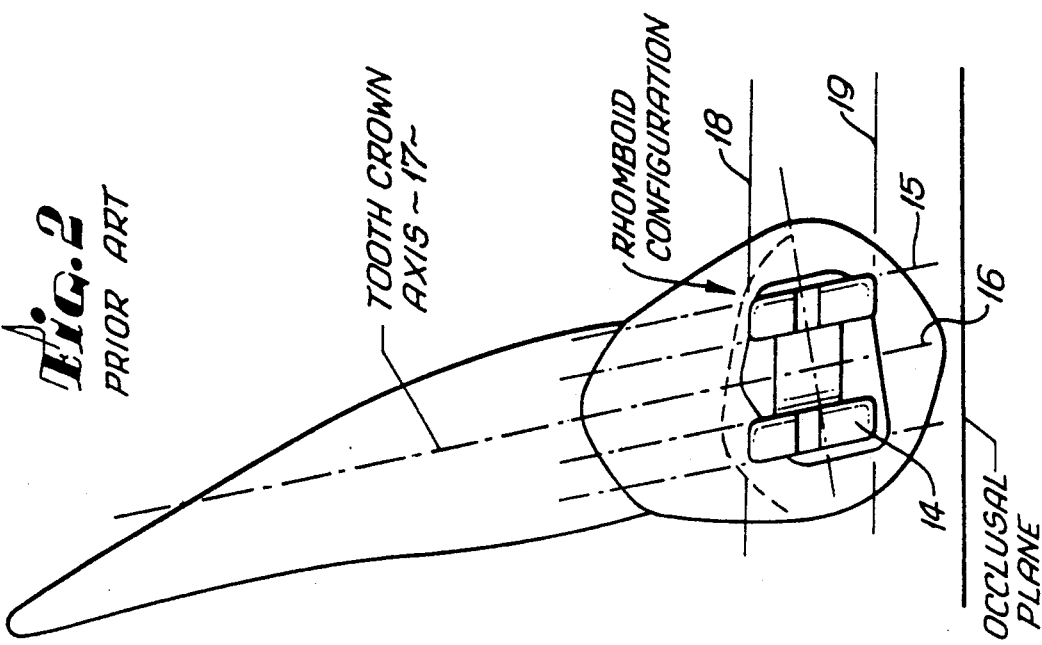
FIG. 2 is a front elevational view of a cuspid having a prior art bracket mounted thereon.

In FIG. 2 there is disclosed a prior art bracket 14, heretofore disclosed, wherein the bracket 14 discloses a rhomboidal configuration 15. Although, the prior art teaches a sight line 16 along tooth crown axis 17 and occlusal sight lines 18, 19 parallel to the occlusal plane, it fails to teach or suggest sight lines that more accurately allow alignment and positioning of the bracket on the tooth especially when the tooth is severely malposed.

A preferred embodiment of the present invention is depicted in FIG. 3 wherein an orthodontic bracket 20 having a trapezoidal configuration is shown. As is known, bracket 20 has a base portion 22 upon which the bracket assembly is permanently fixed. The base portion 22 is constructed to conform to tooth surface 23 and be removably attached to the tooth surface by known means. Generally speaking, the bracket assembly is a cast part made of metallic, ceramic, or other similar substances and is sometimes surface finished to remove sharp edges and burrs. Various methods of manufacturing the bracket are available and the examples given are not intended to be limiting in any manner. The configuration of the base may be such that it imparts torque into the bracket.

In the preferred embodiment as depicted in FIG. 3, the bracket assembly 20 includes a distal tie wing 24 and a mesial tie wing 25 spaced a distance apart and having the same overall configuration and size. The bracket assembly is permanently mounted to the base portion such that when the base portion is mounted on the tooth, it forms a unitary assembly which can only be removed from the tooth when the base portion is removed from the tooth. The bracket assembly and the base portion can be an integral unit, but it is not necessary that they be integral. In this instance, integral is defined to mean all one part, i.e., the base portion and the bracket assembly could be a cast part not requiring any assembly.

The distal tie wing 24 of bracket assembly 20 has a mesial edge 26 and a distal edge 27 which are non-parallel to each other. The distal edge 27 of the distal tie wing forms a distal sight line 27 when extended such that it is substantially parallel to the distal edge 29 of the tooth upon which it is mounted.

The mesial tie wing 25 has mesial and distal edges 30, 31 which are non-parallel to each other. The mesial edge 30 also forms a mesial sight line 32 when extended and it is substantially parallel to the mesial edge 33 of the tooth.

The distal sight line 28 is non-parallel to the mesial sight line 32 such that the two sight lines form the sides of a trapezoid. Further, sight lines 28 and 32, since they are non-parallel, are designed to intersect at a focal point which is located approximately at the tooth root 34. Thus, when the orthodontist is reviewing the x-rays of the patient, he will know the exact location of the tip of the tooth root, and when mounting the bracket, can use sight lines 28 and 32 of the tie wings to align such that they intersect at the focal point, i.e., the tip of the tooth root 34.

The tie wing sight lines 28 and 32 further provide assistance in positioning bracket 20 on the tooth since they are designed to be substantially parallel to the edges of the tooth on which the bracket is mounted. The distal sight line 28 is substantially parallel to the distal edge 29 of tooth 23 while the mesial edge of the mesial tie wing is substantially parallel to the mesial edge 33 of the tooth. By using the tie wing sight lines as they relate to the edges 29 and 33 of the tooth, the orthodontist can more easily position the brackets on the tooth in the mesial-distal direction.

The bracket assembly 20 also includes means for a sight line located midway between the tie wings. In the preferred embodiment, there is shown a V groove 40 which is approximately midway between the distal and mesial tie wings and which is configured to align with tooth axis 41. V groove 40, when extended, provides a sight line 42 that is intended to align with tooth axis 41. Thus, when the orthodontist is mounting the bracket assembly, he can visualize or draw tooth axis 41 along the exposed portion of the tooth to be used as a reference line. A feature of the invention provides for sight line 42 extending through V groove 40 to intersect sight lines 27 and 31 of the mesial and distal tie wings 24, 25 at the focal point. With the aid of X-rays (or whatever imaging means is available to provide the tooth configuration), the orthodontist is able to use the sight lines of the tie wings in conjunction with the sight line of the V groove to accurately align and position the bracket assembly in relation to the tooth configuration.

The bracket assembly 20 also includes an archwire slot 43 which is transverse to tie wings 24, 25 and that has a sight line 44 that is parallel to the sides 45, 46 of archwire slot 43. The sight line 44 is parallel to the occlusal edge 46 of tooth 23 and to occlusal plane formed by the occlusal edges of all of the teeth (as referenced in FIG. 1).

The sight line 44 of the archwire slot has several purposes to facilitate alignment of the bracket on the tooth. First, when the archwire is mounted in the archwire slots of all of the brackets it should be aligned such that the archwire defines a plane that is substantially parallel to the occlusal plane (see FIG. 1). Thus, it is important that the archwire be mounted in the archwire slot of each of the bracket assemblies on various teeth such that it defines a plane parallel to the occlusal plane. If one or more of the archwire slots are misaligned in relation to each other, this would require removal of the bracket assembly from the tooth which is time consuming and costly for the orthodontist. If the archwire slot is only slightly misaligned, this may go undetected by the orthodontist and cause unplanned or undesired movement of the tooth causing further problems.

Secondly, sight line 44 is parallel to occlusal edge 46 of the tooth thus providing a reference point for mounting the bracket assembly along tooth axis 41.

Another aspect of the invention concerns the occlusal edges of mesial and distal tie wings 24, 25. The tie wings are so designed such that occlusal edges 50, 51, when extended, provide a sight line 52 that is parallel to sight line 44 of the archwire slot 43 and further, it is parallel to the tooth edge 46 and the occlusal plane. Thus, the sight line of the occlusal edge provides a further reference point in aligning the bracket along the tooth axis 41.

The bracket assembly 20 provides a trapezoidal configuration which is defined by the sight lines described above. The sight lines 27 and 31 of the tie wings, the occlusal edge sight line 52, and the archwire slot sight line 44 form the sides of a trapezoid that conforms with the trapezoidal configuration of the teeth upon which the bracket assembly is mounted. Specifically, the bracket is particularly adaptable for mounting on the upper central, upper lateral, upper cuspid, upper bicuspid, lower anterior, and lower second bicuspid. The bracket assembly can be mounted on other teeth in the mouth and is not limited to those enumerated. The trapezoidal design lends itself particularly to the enumerated teeth.

Due to the configuration of the bracket assembly, the tie wings are shaped such that they are not the same from the occlusal to the gingival wing. Thus, the bracket is much easier to identify and it would be nearly impossible to mount a bracket incorrectly by placing an occlusal wing bracket on the gingival wing.

As shown in FIG. 4, sight line 60 of V groove 61 intersects the sight line 62 of archwire slot 63 at an angle that is equal to the amount of tip required for that particular tooth. Thus, for the various teeth to which the bracket assembly is particularly adapted, the angle between sight line 60 of the V groove and sight line 62 of the archwire slot ranges anywhere from 90° (perpendicular to each other where no tip is required) to approximately 75°, depending upon the amount of tip required for a particular tooth. By way of example, on a tooth requiring 5° of tip, the angle between sight line 60 of the V groove and sight line 62 of the archwire slot would be 85°.

FIG. 5 depicts a bracket assembly 70 requiring 0° of tooth tip. The tooth axis 71 and sight line 72 of V groove 73 align and the angle between sight line 72 and sight line 74 of the archwire slot is 90°. Thus, no tipping of tooth 75 is required.

Another embodiment of the present invention is shown in FIG. 6 where bracket assembly 80 is mounted as previously described on upper central tooth 81. Bracket assembly 80 includes single tie wing 82 having mesial and distal edges 83, 84 that are non-parallel to each other. When extended, edges 83, 84 form mesial and distal sight lines 85, 86 that intersect at a focal point at the root tip 88. Sight lines 85 and 86 are substantially parallel to mesial and distal edges 89, 90 of tooth 81. When mounting bracket 80, the orthodontist will use sight lines 85, 86 to position the bracket in relation to tooth edges 89, 90.

Bracket 80 also has a V groove 91 that forms a sight line 92 when extended. Sight line 92, which is coextensive with tooth axis 93, intersects sight lines 85, 86 at the focal point. As described above for a double tie wing, these sight lines assist the orthodontist in aligning and positioning the bracket on the tooth.

Bracket 80 also includes a sight line 93 extending midway between the sides 94, 95 of archwire slot 96. Bracket edge 97, when extended, forms sight line 98 which is parallel to sight line 93 and tooth edge 99. Again, as previously described, these sight lines assist in aligning and positioning the bracket when mounting.

The various sight lines 85, 86, 93 and 98 form a trapezoidal configuration that conforms to the tooth configuration upon which bracket 80 is mounted to assist in mounting as described.

The embodiments described herein are intended as examples only and not as limiting in any manner the spirit and scope of the invention. The focal point referred to herein is intended to be substantially at the tip of the tooth root. However, the focal point could be located at other points along the tooth axis and still be within the spirit and scope of the invention.

What we claim is:

1. An orthodontic bracket having a trapezoidal configuration for mounting on a tooth comprising:
   a single tie wing having non-parallel mesial distal edges,
   the mesial and distal edges of the tie wing forming sight lines which intersect at a focal point located at the tip of the tooth root,
   the sight lines of the mesial and distal edges for aligning and positioning the bracket in relation to the mesial and distal edges of the tooth,
   said edges of the mesial and distal tie wing being non-parallel to the tooth axis,
   an archwire slot having a sight line midway between the sides of said slot and parallel to the occlusal plane,
   the tie wing having an occlusal edge forming a sight line that is substantially parallel to the sight line of the archwire slot and the occlusal edge of the tooth,
   the sight lines of the occlusal edge and archwire slot for aligning and positioning the bracket in relation to the occlusal edge of the tooth.

2. An orthodontic bracket having a trapezoidal configuration for ease of positioning and aligning the bracket on a tooth, the bracket comprising:
   a bracket assembly having a base portion,
   a pair of tie wings mounted on the base portion with an archwire slot located transverse to the tie wings,
   the archwire slot having a sight line midway between the sides of said slot and parallel to the occlusal edge of the tooth,
   a distal tie wing having non-parallel mesial and distal edges and an occlusal edge substantially parallel to the sight line of the archwire slot,
   a mesial tie wing having mesial and distal edges and an occlusal edge substantially parallel to the sight line of the archwire slot,
   at least one edge of the distal tie wing being non-parallel to one edge of the mesial tie wing,
   means for providing a tooth axis sight line disposed substantially midway between the distal and mesial tie wings for aligning the bracket with the tooth axis,
   said edges of the mesial and distal tie wings being non-parallel to the tooth axis,
   the non-parallel edges of the tie wings form a pair of sight lines for intersecting with the tooth axis sight line at a focal point at the tip of the tooth root,
   the occlusal edges of the tie wings and the archwire slot forming parallel sight lines that are parallel to the occlusal edge of the tooth.

3. An orthodontic bracket having a trapezoidal configuration for ease of positioning and aligning on the tooth, a bracket comprising:
   a bracket assembly having an archwire slot with a sight line midway between the sides of said slot and parallel to the occlusal edge of the tooth,
   a distal tie wing having parallel mesial and distal edges and an occlusal edge substantially parallel to the sight line of the archwire slot, a mesial tie wing having parallel mesial and distal edges and an occlusal edge substantially parallel to the sight line of the archwire slot, the mesial and distal edge of the distal tie wing being non-parallel to the mesial and distal edges of the mesial tie wing, said edges of the mesial and distal tie wings being non-parallel to the tooth axis, means for providing a tooth axis sight-line disposed substantially between the distal and mesial tie wings for aligning the bracket with the tooth axis and intersecting the focal point, the distal edge of the distal tie wing and the mesial edge of the mesial tie wing forming a pair of sight lines that intersect at a focal point, the occlusal edges of the tie wings form a sight line parallel to the sight line of the archwire slot and the occlusal edge of the tooth for ease of bracket alignment and positioning.

* * * * *